United States Patent [19]

Lennon

[11] Patent Number: 4,672,135

[45] Date of Patent: Jun. 9, 1987

[54] CATALYTIC PROCESS FOR PRODUCING SILAHYDROCARBONS

[75] Inventor: Patrick J. Lennon, Clayton, Mo.

[73] Assignee: Monsanto Company, St. Louis, Mo.

[21] Appl. No.: 858,975

[22] Filed: May 2, 1986

[51] Int. Cl.$^4$ ............... C07F 7/08; C07F 7/10; C07F 7/18
[52] U.S. Cl. .................. 556/480; 556/413; 556/430; 556/455; 556/456
[58] Field of Search ............ 556/480, 430, 413, 455, 556/456

[56] References Cited

U.S. PATENT DOCUMENTS

| | | | |
|---|---|---|---|
| 2,212,992 | 8/1940 | Sowa | 556/480 X |
| 2,380,057 | 7/1945 | McGregor et al. | 556/480 |
| 2,426,122 | 8/1947 | Rust et al. | 556/480 |
| 2,813,886 | 11/1957 | Ramsden | 556/480 |
| 2,813,887 | 11/1957 | Ramsden | 556/480 |
| 2,872,471 | 2/1959 | Ramsden et al. | 556/480 |
| 3,426,087 | 2/1969 | Asuby | 556/480 X |

*Primary Examiner*—Paul F. Shaver
*Attorney, Agent, or Firm*—Thomas E. Kelley; Charles E. Krukiel; Arthur E. Hoffman

[57] ABSTRACT

Silahydrocarbons such as tetraorganosilanes prepared from halo-substituted silanes and an organomagnesium compound in the presence of a catalytically effective amount of a thiocyanate.

31 Claims, No Drawings

CATALYTIC PROCESS FOR PRODUCING SILAHYDROCARBONS

BACKGROUND OF THE INVENTION

The invention relates to processes for producing silahydrocarbons.

Organosilicon fluids are well known and used as additives or substitutes for hydrocarbon oil based hydraulic fluids. For instance, hydraulic fluids comprising alkyl substituted silanes exhibit desirable properties even when subject to wide variations in temperature, see U.S. Pat. No. 2,872,471 and U.S. Pat. No. 2,962,335 which disclose hydraulic fluids comprising tetraalkylsilanes in which the alkyl groups are the same or different.

As demands increase for fluids having greater versatility and particularly oxidative stability at elevated temperatures in oils, greases, and hydraulic fluids, more attention has been directed toward silahydrocarbons, such as tetraalkylsilanes.

A disadvantage in the preparation of silahydrocarbons such as tetraalkylsilanes is the excessive time required for reaction. U.S. Pat. No. 4,367,343 describes reactions for preparation of tetraalkylsilanes requiring 18 to 40 hours to complete. Similarly an article by Tamborski et al, *Ind. Eng. Chem. Prod. Res. Dev.*, (1983) 22, 172–178 describing reactions requiring 18–48 hours to complete.

The heretofore known methods of preparing tetraalkylsilanes are time consuming and therefore costly. Accordingly, an object of this invention is to provide methods of preparing tetraalkylsilanes with substantial reductions in reaction time.

SUMMARY OF THE INVENTION

According to this invention, silahydrocarbons such as tetraorganosilanes are prepared from halo-substituted silanes and an organomagnesium compound in the presence of a catalytically effective amount of a thiocyanate.

DETAILED DESCRIPTION OF THE INVENTION

The term silahydrocarbon, as used herein, means compounds of silicon substituted with at least one, and often three or four, hydrocarbon groups. Silahydrocarbons include tetraalkylsilanes which may be symmetrically substituted, such as $Si(CH_3)_4$, or non-symmetrically substituted, such as $CH_3Si(C_{12}H_{25})_3$. Silahydrocarbons include organosilicon compounds having a single silicon atom, such as tetraalkylsilane, tetraarylsilane or tetra(alkyl aryl)silanes. Silahydrocarbons also include organo silicon compounds having more than one silicon atom such as organo-substituted 1,2-disilylethane, e.g. hexaalkyl-1,2-disilylethane, hexaaryl-1,2-disilylethane and the like.

As is well known, the properties of the silahydrocarbons, such as vapor pressure, boiling point, viscosity and thermal stability may be controlled by the selection of the hydrocarbon substituents. For instance, with alkyl substituted silanes as the length of the carbon chain increases, the boiling point normally increases. Also, viscosity, pour point and crystallizing point are strongly influenced by the molecular size and shape of the silahydrocarbon molecule. Preferred silahydrocarbons with optional properties, e.g. for use as hydraulic fluids, can comprise mixed organo substituents or blends of mixed organo substituents. For instance, such silahydrocarbons can comprise alkyl, aryl or alkaryl substituted silanes; mixed alkyl, aryl or alkaryl substituted silanes or mixtures thereof.

One preferred silahydrocarbon based hydraulic fluid comprises a blend of mixed alkyl substituted silanes where the alkyl substituents are methyl, octyl and decyl groups (HYDRAULIC BLEND). Such HYDRAULIC BLEND comprises methyl trioctylsilane (about 35%), methyldioctyldecylsilane (about 45%), methyloctyldidecylsilane (about 18%) and methyltridecylsilane (about 2%).

The term "halo-substituted silanes", as used herein means silicon compounds, including organosilicon compounds having at least one halogen moiety, e.g. chloride, substituted on a silicon atom. For instance, halo-substituted silanes having a single silicon atom can be represented by the structural formula $SiX_nR_{4-n}$; where X is halogen, e.g. chloride; R is hydrogen, alkyl such as methyl, butyl, octyl and the like, aryl such as phenyl, alkaryl such as benzyl, alkoxy such as methoxy, ethoxy and the like, amine, siloxy including substituted siloxy such as halo-substituted siloxy; and n is an integer, generally 1–3. Preparation of trihalo-substituted silanes, a useful and convenient material for the process of this invention, is well known. See U.S. Pat. No. 2,654,771, hereby incorporated by reference, showing, e.g. in Example 1, a preparation of trihalo-substituted silanes from silicon chloride and methylmagnesium chloride.

In the process of this invention halo-substituted silanes are mixed with organomagnesium compounds which can react to provide organic moiety substitution of such halo-substituted silanes.

Organomagnesium compounds can be Grignard reagents, or mixtures of Grignard reagents, represented by the structural formula RMgX, where X is a halogen such as bromine, and R is alkyl such as octyl, cycloalkyl such as cyclohexyl, aryl such as phenyl, aralkyl such as 2-phenyl ethyl, alkaryl such as tolyl or a heterocyclic group such as pyridyl. The preparation of Grignard reagents is well known. For instance, Grignard reagents are typically prepared in an anhydrous ether medium by the addition of an alkyl or aryl halide to metallic magnesium. Commonly used ethers include diethyl ether and THF.

Organomagnesium compounds can also be diorganomagnesium, or mixtures of diorganomagnesium, represented by the structural formula $R_2Mg$, where R is an alkyl, aryl, alkaryl or other group as described above with respect to Grignard reagent. Diorganomagnesium can be prepared by disproportionation of a Grignard reagent, e.g. by reacting a Grignard reagent with dioxane. More preferably, where R is alkyl, aralkyl or other substituted alkyl, diorganomagnesium can be prepared by methods disclosed in U.S. Pat. No. 4,329,301, and European Patent publication No. EP 0 157 297 Al, both of which are incorporated herein by reference. Such synthesis is typically conducted in two steps. Magnesium is first hydrogenated in the presence of a catalyst, e.g. anthracene and chromium chloride under mild conditions, e.g. about 20° (temperatures reported herein are in Celsius), in an anhydrous ether, e.g. THF. Magnesium hydride is then caused to react with an alpha-olefin in the presence of a catalyst, e.g. zirconium halide, at elevated temperature to provide a diorganomagnesium, e.g. dialkylmagnesium. Such a two-step procedure is illustrated in the following equations:

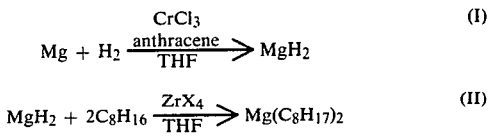

$$Mg + H_2 \xrightarrow[THF]{CrCl_3, \text{anthracene}} MgH_2 \quad (I)$$

$$MgH_2 + 2C_8H_{16} \xrightarrow[THF]{ZrX_4} Mg(C_8H_{17})_2 \quad (II)$$

The magnesium hydride is added across the double bond of the olefin, e.g. 1-octene, to produce dioctylmagnesium. Zirconium halide catalysts employed in this reaction are highly specific, producing only straight chain dialkylmagnesium. Such diorganomagnesium is believed to be more reactive than Grignard reagent and is generally preferred over Grignard reagent because there are two organo groups with each magnesium atom rather than one alkyl group per magnesium atom as in the Grignard reagent. Moreover, diorganomagnesium is often preferred because it can be made from an olefin rather than an alkyl halide. In some cases blends of olefins can be used to prepare mixed dialkyl magnesium. For instance in the preparation of HYDRAULIC BLEND silahydrocarbons, the preferred dialkylmagnesium is prepared from a mixture of octene (70 mol %) and decene (30 mol %).

According to the processes of this invention silahydrocarbons are preferably prepared by combining halo-substituted silanes and organomagnesium compounds in a reaction medium comprising a Grignard stable solvent. The phrase "Grignard stable solvent", as used herein, means an organic compound that is substantially unreactive with a Grignard reagent or mixture of such compounds. Such compounds include ethers, for instance alkyl ethers such as diethyl ether, dipropyl ether, ethyl propyl ether, ethyl methyl ether, dibutyl ether, dioctyl ether and the like; diaryl ethers, such as diphenyl ether; alkyl aryl ethers, such as anisole and cyclic ethers such as tetrahydrofuran (THF). Other compounds include alkyl, aryl or aralkyl compounds devoid of protons attached to electronegative elements, such as oxygen, nitrogen, sulfur or triple bonded carbon; such other compounds may include alkanes, such as octane, decane, and the like, including cycloalkanes, such as cyclohexane, olefins, such as octene, heptene and the like; aromatic compounds, such as benzene, toluene, and halogenated aromatic compounds such as chlorobenzene.

In one embodiment of this invention, e.g. as illustrated in more detail in Example 1 below, dioctylmagnesium is caused to react with methyltrichlorosilane in the presence of a catalytically effective amount of silver thiocyanate. After less than two hours, the catalyzed process of this invention resulted in about 80% of the methyltrichlorosilane being converted to methyltrioctylsilane (MTOS).

The high yields resulting from reactions of this invention are distinguished from the relatively low yields afforded by the prior art processes conducted without a catalyst of this invention, e.g. as illustrated in more detail in Example 2 below. Even after extended reaction time of more than 16 hours, such prior art process yielded only about 36% MTOS, about 5% of the intermediate methyldioctylsilyl chloride and large quantities, e.g. about 43%, of the by-product methyldioctylsilyl hydride.

The processes of this invention are conducted in the presence of a thiocyanate, preferably in the presence of a catalytically effective amount of a thiocyanate. By "thiocyanate" is meant a compound containing at least one thiocyanato group. In many embodiments of the processes of this invention the thiocyanate is present in a catalytically effective amount such that the molar ratio of thiocyanate to amount of halo-substituted silane added to the reaction medium is less than about 0.2:1. In many other embodiments the thiocyanate is present in a catalytically effective amount such that the molar ratio of the thiocyanate to the silane is less than about 0.1:1 or lower say about 0.05:1. In even other cases the formation of silahydrocarbons is catalytically effected by lower levels of thiocyanate, e.g. where such molar ratio is less than about 0.03:1, say about 0.01:1, or even lower.

As stated above, and in accordance with this invention, a halo-substituted silane is caused to react with an organomagnesium compound in the presence of a catalytically effective amount of a thiocyanate. Exemplary thiocyanates found to be catalytically effective in the process of this invention include silver thiocyanate, potassium thiocyanate, lithium thiocyanate, copper (cuprous and cupric) thiocyanates, calcium thiocyanate, barium thiocyanate, manganese (II) thiocyanate, magnesium thiocyanate, cobalt (II) thiocyanate, and lead (II) thiocyanate. Other thiocyanate compounds include quaternary ammonium compounds, such as tetra-n-butyl ammonium thiocyanate. It is reasonable to assume that other noninterfering thiocyanates, or compounds which may produce thiocyanato group in an ionic form in the reaction medium, are expected to be catalytically effective in processes of this invention. Other effective materials can comprise thiocyanato-containing anion exchange resin. Despite the effectiveness of many thiocyanates, it has been demonstrated that certain thiocyanates, e.g. ferric thiocyanate, and mercuric tetrathiocyanato cobaltate (II), are not catalytically effective in the production of silahydrocarbons.

The process of this invention can be conducted generally at any desired temperature which the solvent is in a liquid state, for instance at any temperature below the boiling point of the solvent. Although not generally desirable, higher temperatures can be used, e.g. with reflux. The lower limit of process temperature is often governed by the solubility of reactant materials. Since the process of this invention comprises an exothermic reaction, cooling is often employed. Conveniently desirable reaction temperatures range from as low at about 0° or lower, for instance as low as about −20°, to as high as about 50° or higher. In many cases the reaction is preferably carried out no higher than about 60°–70°.

Conveniently, the halo-substituted silanes are often added to a medium comprising solvent, excess organomagnesium compound and catalyst over a period of time to avoid excessive elevation of temperature of the reaction medium. To provide reaction control it is generally considered desirable, although not necessary, practice to maintain a substantially uniform temperature. Of course process conditions will vary according to the particular silahydrocarbon being prepared, the particular organomagnesium compound being employed and/or the particular catalyst used.

Upon completion of the reaction e.g. as indicated by the termination of exothermic heat of reaction, the silahydrocarbon products can be recovered from the reaction medium by first neutralizing any remaining reactants. Water, e.g. chilled water or a water/ice slurry, is conveniently added to the reaction medium to neutralize any unreacted magnesium compound, e.g. magnesium, magnesium hydride, diorganomagnesium, Grignard reagent or magnesium chloride. A mineral acid, e.g. HCl, can be also conveniently added to assist in neutralizing reactants and to provide an acidic medium, e.g. to minimize foaming.

It is generally preferred to avoid the addition of water to anything but a minimal amount of partially-reacted halo-silanes. In this regard, the hydration reaction of water with alkyl trichlorosilane can result in a crosslinked polymer, with dialkyl dichlorosilanes, in a siloxane polymer; and with trialkylchlorosilane, in a silanol which can dimerize. Those hydration products can also react among themselves to form other products. To facilitate the separation of silahydrocarbons from the reaction medium the production of such silane hydration products can be minimized by utilizing an excess of the organomagnesium compound and by adding the halosilane incrementally to the organomagnesium reaction medium.

The mixture of water (and optionally mineral acid) and reaction medium can be separated into an organic phase comprising silahydrocarbon and an aqueous phase which optionally can be extracted, e.g. with an organic liquid such as toluene, to remove residual silahydrocarbon. The organic phase is often conveniently filtered, e.g. through diatomaceous earth, to remove inorganic salts and other solid impurities, e.g. cyanide catalyst or catalyst from the production of organomagnesium compound orpolymerized byproducts. The silahydrocarbon is conveniently recovered from the other organic phase materials, e.g. Grignard solvents such as THF, residial olefins and optional extractants such as toluene by stripping, e.g. at reduced pressure and/or elevated temperature. Stripping can be effected in a number of stages. Low boilers such as Grignard solvents and olefins can be removed under moderate stripping conditions; while high boilers such as anthracene (which is often residual from the production of diorganomagnesium and manifested by fluorescence) and silane by products such as trialkylsilane hydride can be removed under generally more severe stripping conditions sucn as low pressure, e.g. about 0.5 mm pressure. It has been found desirable in some instances to treat recovered silahydrocarbons in active alumina columns to effect removal of residual anthracene and/or color bodies, e.g. compounds exhibiting yellow color and fluorescence.

The following examples will illustrate various embodiments of the process of this invention, without intending to imply any limitation to the scope of the invention. While equally applicable to the preparation of other silahydrocarbons, the process improvement of the instant invention will be described in principal part in the following examples through the description of the preparation of methyltri-n-octylsilane (MTOS). Yields reported in the following examples were determined by gas chromatography and are based on the amount of trichloromethylsilane.

EXAMPLE 1

This example illustrates the preparation MTOS from a dialkylmagnesium compound, an alkyltrihalosilane and a thiocyanate catalyst.

Dioctylmagnesium was prepared essentially as described in Example 12 of U.S. Pat. No. 4,329,301 to provide a 0.78M solution of dioctylmagnesium in THF.

0.73 g (2.4 mmoles) of dry docosane, an effectively inert substance used as standard for gas chromatographic quantitation, was added to 10 ml of the solution of dioctylmagnesium (7.8 mmoles). The solution was stirred in a 0° bath under argon. 0.029 g (0.18 mmoles) of silver thiocyanate was added. 0.4 ml of a 0.85M solution of methyltrichlorosilane ($MeSiCl_3$) (3.4 mmoles) in THF was added over a 40 minute period. The stirred solution was held at 10° for an additional 20 minutes, removed to room temperature and stirred for an additional 40 minutes. The yield of MTOS based on added $MeSiCl_3$ was about 79%. After further mixing at room temperature for about an additional 16 hours (i.e. overnight), the yield of MTOS was about 82%. The molar ratio of thiocyanate to $MeSiCl_3$ was about 0.05:1. The results are recapitulated in Table 1.

EXAMPLE 2

This example illustrates comparative results when the procedure of Example 1 is carried out without a thiocyanate catalyst.

0.73 g (2.4 mmoles) of dry docosane was added to 10 ml of a 0.78M solution of dioctylmagnesium (7.8 mmoles) in THF.

0.4 ml of neat $MeSiCl_3$ (3.4 mmoles) was added over a 60 minute period at 0°. After an additional 3.5 hours at room temperature the yield of MTOS based on added trichloromethylsilane was about 31%. After 16 hours at room temperature, the yield of MTOS was about 36%, while the yield of the intermediate product dioctylmethylsilylchloride was about 5% and the yield of the byproduct dioctylmethylsilane was about 43%. The results are recapitulated in Table 1.

EXAMPLES 3–4

These examples illustrate the process of this invention where thiocyanate compounds are used to catalyze the reaction of an organomagnesium compound, i.e. dioctyl-magnesium ($R_2Mg$), with a halosilane, i.e. $MeSiCl_3$. Two 10 ml volumes of 0.78M solution of dioctylmagnesium (7.8 mmoles) in THF were cooled to 0° as in Example 1. Thiocyanate catalyst was added as indicated in Table 1. 0.4 ml of neat $MeSiCl_3$ was added to provide a reaction mixture which was stirred at 0° for about 1 hour; the reaction mixture was then allowed to warm to room temperature (RT) and stirring often continued for about 16 hours (i.e. overnight). Analysis by gas chromatography provided yields of MTOS at the times indicated in Table 1.

Also reported in Table 1 is the molar ratio of catalyst to halosilane.

TABLE 1

| | Catalyst | | | | Reaction Time (hours) | | |
|---|---|---|---|---|---|---|---|
| Ex. | Species | Molar Ratio | $R_2Mg$ (mmol) | $MeSiCl_3$ (mmol) | 0° | RT | Yield |
| 1. | AgSCN | 0.05 | 7.8 | 3.4 | 1 | 0.7 | 79% |
| 2. | None | | 7.8 | 3.4 | 1 | 3½ | 31% |
| | | | | | | 16+ | 36% |
| 3. | Bu4NSCN | 0.05 | 7.8 | 3.4 | 1 | 3.2 | 92% |
| | | | | | | 16+ | 90% |
| 4. | KSCN | 0.05 | 7.8 | 3.4 | 1 | 3.4 | 79% |
| | | | | | | 16+ | 78% |

EXAMPLES 5–7

These examples illustrate the catalytic effect of copper (cuprous and cupric) thiocyanates in the processes of this invention. The procedures of Examples 1–4 were repeated except for the use of catalysts as indicated in Table II and the reaction being carried out in 8 ml volumes of solutions of dioctylmagnesium (R$_2$Mg) in THF. The specific reaction conditions and results are reported in Table II.

TABLE II

| | Catalyst | | R$_2$Mg | MeSiCl$_3$ | Reaction Time (hours) | | Yield |
|---|---|---|---|---|---|---|---|
| Ex. | Species | Molar Ratio | (mmol) | (mmol) | 0° | RT | |
| 5. | CuSCN | 0.05 | * | 3.4 | 1 | 2½ | 73% |
| 6. | Cu(SCN)$_2$ | 0.05 | * | 3.4 | 1 | 2¾ | 81% |
| 7. | None | — | * | 3.4 | 1 | 3 | 14% |

*Excess with respect to MeSiCl$_3$.

EXAMPLES 8–10

These examples illustrate the catalytic effect of calcium and barium thiocyanate in the processes of this invention. The procedures of Examples 1-4 were repeated except for the use of catalyst as indicated in Table III and the reaction being carried out in 11 ml volumes of 0.63M solution of the dioctylmagnesium (R$_2$Mg) in THF. The specific reaction conditions and results are reported in Table III.

TABLE III

| | Catalyst | | R$_2$Mg | MeSiCl$_3$ | Reaction Time (hours) | | Yield |
|---|---|---|---|---|---|---|---|
| Ex. | Species | Molar Ratio | (mmol) | (mmol) | 0° | RT | |
| 8. | Ca(SCN)$_2$ | 0.05 | 6.9 | 3.4 | 1 | 0.8 | 73% |
| | | | | | | 16+ | 75% |
| 9. | Ba(SCN)$_2$ | 0.05 | 6.9 | 3.4 | 1 | 0.5 | 20% |
| | | | | | | 16+ | 71% |
| 10. | None | — | 6.9 | 3.4 | 1 | 0.8 | 12% |
| | | | | | | 16+ | 32% |

EXAMPLES 11–15

These examples further illustrate the catalytic effect of manganese, magnesium and cobalt thiocyanates and thiocyanate substituted anion exchange resins (Resin+SCN$^-$) in the processes of this invention. The procedures of Examples 1-4 were repeated except for the use of catalysts as indicated in Table IV and the reaction being carried out in 12 ml volumes of 0.56M solutions of dioctylmagnesium (R$_2$Mg) in THF. The specific reaction conditions and results are reported in Table IV.

TABLE IV

| | Catalyst | | R$_2$Mg | MeSiCl$_3$ | Reaction Time (hours) | | Yield |
|---|---|---|---|---|---|---|---|
| Ex. | Species | Molar Ratio | (mmol) | (mmol) | 0° | RT | |
| 11. | Mn(SCN)$_2$ | 0.05 | 6.8 | 3.4 | 1 | 0.8 | 55% |
| | | | | | | 16+ | 83% |
| 12. | Mg(SCN)$_2$ | 0.05 | 6.8 | 3.4 | 1 | 0.6 | 41% |
| | | | | | | 16+ | 70% |
| 13. | Co(SCN)$_2$ | 0.05 | 6.8 | 3.4 | 1 | 1.5 | 30% |
| | | | | | | 16+ | 43% |
| 14. | Resin + SCN$^-$ | 0.05 | 6.8 | 3.4 | 1 | 16+ | 47% |
| 15. | None | — | 6.8 | 3.4 | 1 | 1 | 8% |
| | | | | | | 16+ | 20% |

EXAMPLES 16–18

These examples illustrate the catalytic effect of lithium and lead thiocyanate in the processes of this invention. The procedures of Examples 1-4 were repeated except for the use of catalysts as indicated in Table V and the reaction being carried out in 11 ml volumes of 0.65M solutions of dioctylmagnesium (R$_2$Mg) in THF. The specific reaction conditions and results are reported in Table V.

TABLE V

| | Catalyst | | R$_2$Mg | MeSiCl$_3$ | Reaction Time (hours) | | Yield |
|---|---|---|---|---|---|---|---|
| Ex. | Species | Molar Ratio | (mmol) | (mmol) | 0° | RT | |
| 16. | LiSCN | 0.05 | 7.2 | 3.4 | 1 | 0.5 | 32% |
| | | | | | | 16+ | 71% |
| 17. | Pb(SCN)$_2$ | 0.5 | 7.2 | 3.4 | 1 | 0.5 | 40% |
| | | | | | | 16+ | 71% |
| 18. | None | — | 7.2 | 3.4 | 1 | 0.8 | 12% |
| | | | | | | 16+ | 20% |

EXAMPLES 19 AND 20

These examples illustrate the catalytic effect of trimethylsilylisothiocyanate (Me$_3$SiNCS) in the process of this invention. The procedures of Examples 1-4 were repeated except for the use of catalyst as indicated in Table VI and the reaction being carried out in 12 ml volumes of 0.61M solutions of dioctylmagnesium (R$_2$Mg) in THF. The specific reaction conditions and results are reported in Table VI.

TABLE VI

| | Catalyst | | R$_2$Mg | MeSiCl$_3$ | Reaction Time (hours) | | Yield |
|---|---|---|---|---|---|---|---|
| Ex. | Species | Molar Ratio | (mmol) | (mmol) | 0° | RT | |
| 19. | Me$_3$SiNCS | 0.05 | 7.4 | 3.4 | 1 | 1½ | 69% |
| | | | | | | 16+ | 77% |
| 20. | None | — | 7.4 | 3.4 | 1 | 4.6 | 30% |
| | | | | | | 16+ | 33% |

EXAMPLE 21

This example illustrates the production of silahydrocarbons useful as HYDRAULIC BLEND.

A 1.08M solution of dialkylmagnesium in THF was prepared from a blend of 1-octene (70 mol %) and 1-decene (30 mol %). 27.2 g of cuprous cyanide (0.3 mol) was added to 8.5 liters of the dialkylmagnesium at about 10° under an argon blanket in a 5 gallon stirred reactor. MeSiCl$_3$ was added slowly to maintain the reaction medium below about 15°. After addition of 715 ml of the MeSiCl$_3$ (6.1 mol) the reaction medium temperature was maintained at 20°-25° for about 1 hour. The reaction medium was then cooled to about 10° and quenched with 2 liters of water, added in small portions to avoid excess exothermic hydration of the unreacted materials. The resulting mixture was then transferred slowly into a container of crushed ice and concentrated muriatic acid (about 5 kg ice and 3 liters of muriatic acid). After stirring for several hours, the mixture was separated into an organic phase and an aqueous phase. The organic phase was filtered through diatomaceous earth. THF and residual olefin were removed from the organic phase by distillation. Further filtration removed precipitated solids. Silahydrocarbons were recovered by distillation in a packed column at about 0.7 mm pressure, liquid temperature of 243°-290°, and vapor temperature of 197°-250°. Yellow and fluorescent color was removed by passing the silahydrocarbon through a neutral alumina (activity 1) bed. The yield of a mixture of methyltrioctylsilane, methyldioctyldecylsilane, methyloctyldidecylsilane and methyltridecylsilane was about 2 kg, about 79% based on MeSiCl$_3$.

EXAMPLE 22

This example illustrates the process of this invention in the production of HYDRAULIC BLEND.

The procedures of Example 21 are repeated except that cuprous cyanide is replaced with silver thiocyanate as the catalyst and that ventilation is required to carry away hydrogen sulfide gas liberated during quenching with muriatic acid. Similarly, good yields of silahydrocarbons result.

What is claimed is:

1. A process for producing silahydrocarbons comprising mixing in solution a halo-substituted silane, an organomagnesium compound and a thiocyanate compound.

2. The process of claim 1 wherein said thiocyanate compound is present such that the molar ratio of thiocyanate to halo-substituted silane is less than about 0.2:1.

3. The process of claim 1 wherein said organomagnesium compound comprises a Grignard reagent.

4. The process of claim 3 wherein said process is carried out in a Grignard stable solvent.

5. The process of claim 4 wherein said solvent comprises an ether.

6. The process of claim 5 wherein said ether comprises tetrahydrofuran.

7. The process of claim 1 wherein said halo-substituted silane is an organotrihalosilane.

8. The process of claim 1 wherein said organomagnesium compound comprises diorganomagnesium.

9. The process of claim 8 wherein said process is carried out in a Grignard stable solvent.

10. The process of claim 9 wherein said solvent comprises an ether.

11. The process of claim 10 wherein said ether comprises tetrahydrofuran.

12. A process for producing silahydrocarbons by reacting a halo-substituted silane with an organomagnesium compound comprising effecting said reacting in the presence of a catalytically effective amount of a thiocyanate.

13. The process of claim 12 wherein said reacting is carried out in a Grignard stable solvent.

14. The process of claim 13 wherein said solvent comprises an ether.

15. The process of claim 14 wherein said ether comprises tetrahydrofuran.

16. The process of claim 12 wherein said organomagnesium compound comprises diorganomagnesium or a Grignard reagent.

17. The process of claim 16 wherein said organomagnesium compound comprises dialkylmagnesium, diarylmagnesium, an alkyl Grignard reagent, an aryl Grignard reagent, or mixtures thereof.

18. The process of claim 12 wherein halo-substituted silane is added to a solution of organomagnesium compound.

19. The process of claim 18 wherein the molar ratio of said thiocyanate to reacted halo-substituted silane is less than about 0.2:1.

20. A process comprising adding a halo-substituted silane to a solution of organomagnesium compound containing a thiocyanate.

21. The process of claim 20 wherein said solution comprises an ether solvent.

22. The process of claim 21 wherein said ether solvent comprises tetrahydrofuran.

23. The process of claim 22 wherein said thiocyanate is present in a catalytically effective amount.

24. The process of claim 23 wherein said thiocyanate is present in an amount such that the molar ratio of thiocyanate to amount of halo-substituted silane added is less than about 0.2:1.

25. The process of claim 24 wherein halo-substituted silane is $SiX_nR_{4-n}$, where X is a halogen; R is hydrogen, alkyl, aryl, alkaryl, alkoxy, amine, or siloxy; and n is 1–4.

26. The process of claim 25 wherein said organomagnesium compound is $R_2Mg$ or $RMgX$, when X is halogen; and R is alkyl, aryl, or alkaryl.

27. A process for producing tetraorganosilanes comprising reacting halo-substituted silanes with organomagnesium compounds in the presence of a catalytically effective amount of a thiocyanate.

28. The process of claim 27 wherein said halo-substituted silane is an organotrihalosilane.

29. The process of claim 27 wherein said organomagnesium compound is $R_2Mg$ or $RMgX$, where X is a halogen; and R is alkyl, aryl, or alkaryl.

30. The process of claim 29 wherein said reacting is carried out in a medium comprising an ether.

31. The process of claim 30 wherein said ether comprises tetrahydrofuran.

* * * * *